(12) United States Patent
Imai et al.

(10) Patent No.: US 8,222,409 B2
(45) Date of Patent: Jul. 17, 2012

(54) NITROGEN-CONTAINING HETEROCYCLIC COMPOUND

(75) Inventors: Akira Imai, Kanagawa (JP); Hidekazu Hirose, Kanagawa (JP); Koji Horiba, Kanagawa (JP); Takeshi Agata, Kanagawa (JP); Katsuhiro Sato, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 329 days.

(21) Appl. No.: 12/552,619

(22) Filed: Sep. 2, 2009

(65) Prior Publication Data

US 2010/0234595 A1    Sep. 16, 2010

(30) Foreign Application Priority Data

Mar. 16, 2009  (JP) .................. 2009-062869

(51) Int. Cl.
*C07D 403/14*  (2006.01)
*H01J 1/63*  (2006.01)
*C09K 11/06*  (2006.01)

(52) U.S. Cl. .................. 544/219; 544/180; 428/690

(58) Field of Classification Search .................. 544/219, 544/180
See application file for complete search history.

(56) References Cited

U.S. PATENT DOCUMENTS

| | | | |
|---|---|---|---|
| 7,692,029 B2 * | 4/2010 | Han et al. | 549/59 |
| 8,058,457 B2 * | 11/2011 | Han et al. | 549/59 |
| 2006/0006379 A1 | 1/2006 | Lee et al. | |
| 2006/0076553 A1 | 4/2006 | Lee et al. | |
| 2008/0224130 A1 | 9/2008 | Lee et al. | |
| 2009/0140239 A1 | 6/2009 | Lee et al. | |

FOREIGN PATENT DOCUMENTS

| | | |
|---|---|---|
| JP | A-2003-45662 | 2/2003 |
| JP | A-2006-37098 | 2/2006 |
| JP | A-2006-111854 | 4/2006 |
| JP | A-2006-225428 | 8/2006 |

OTHER PUBLICATIONS

Kojima at al., "Organic field-effect transistors based on heterocyclic co-oligomers containing a pyrazine ring," Chem. Commun., pp. 1430-1432, 2007.

* cited by examiner

*Primary Examiner* — Venkataraman Balasubramanian
(74) *Attorney, Agent, or Firm* — Oliff & Berridge, PLC (57) ABSTRACT

A nitrogen-containing heterocyclic compound is represented by Formula (I): wherein $R^1$ represents a hydrogen atom, a substituted or unsubstituted alkyl group having 1 to 20 carbon atoms, or a substituted or unsubstituted alkoxy group having 1 to 20 carbon atoms; A represents a heterocyclic residue that contains at least one nitrogen atom and forms a six-membered aromatic heterocyclic ring; and n represents an integer of from 1 to 3.

(I)

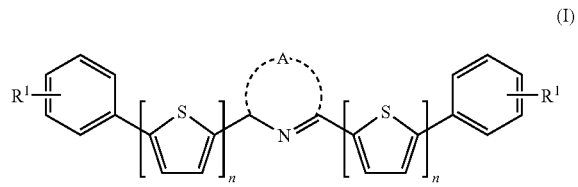

11 Claims, 8 Drawing Sheets

NITROGEN-CONTAINING HETEROCYCLIC COMPOUND

CROSS REFERENCE TO RELATED APPLICATIONS

This application is based on and claims priority under 35 USC 119 from Japanese Patent Application No. 2009-062869, filed on Mar. 16, 2009.

BACKGROUND

1. Technical Field

The present invention relates to a nitrogen-containing heterocyclic compound.

2. Related Art

If generated charges are efficiently received and quickly transferred in organic photoreceptors or organic electronic devices such as organic electroluminescence devices, organic transistors and organic optical memories, the lifespan and performance thereof can be improved. Therefore, the role of charge transporting materials has become important in this regard.

Charge transporting materials are being developed, and attention is being focused on improving characteristics such as charge mobility and charge-injection capability.

Charge transporting materials are required to have various properties such as solubility, film forming ability and heat resistance. For example, for organic electrophotographic photoreceptors, charge transporting materials are required to have high solubility in organic solvents and low residual potential. For organic electroluminescence devices, charge transporting materials are required to have bright emission and to maintain high stability over repeated use.

Well known charge transporting materials for electronic devices include charge transporting polymers typified by polyvinylcarbazole (PVK) and aromatic amine compounds such as N,N-di(m-tolyl)N,N'-diphenylbenzidine, 1,1-bis[N, N-di(p-tolyl)aminophenyl]cyclohexane and 4-(N,N-diphenyl)aminobenzaldehyde-N,N-diphenylhydrazone compounds.

SUMMARY

According to an aspect of the present invention, there is provided a nitrogen-containing heterocyclic compound represented by Formula (I):

(I)

In Formula (I), $R^1$ represents a hydrogen atom, a substituted or unsubstituted alkyl group having 1 to 20 carbon atoms or a substituted or unsubstituted alkoxy group having 1 to 20 carbon atoms; A represents a heterocyclic residue that contains at least one nitrogen atom and forms a six-membered aromatic heterocyclic ring; and n represents an integer of from 1 to 3.

BRIEF DESCRIPTION OF THE DRAWINGS

Exemplary embodiments of the present invention will be described in detail based on the following figures, wherein.

DETAILED DESCRIPTION

In an exemplary embodiment, the nitrogen-containing heterocyclic compound is a compound represented by Formula (I) below.

(I)

In Formula (I), $R^1$ represents a hydrogen atom, a substituted or unsubstituted alkyl group having 1 to 20 carbon atoms or a substituted or unsubstituted alkoxy group having 1 to 20 carbon atoms; A represents a heterocyclic residue that contains at least one nitrogen atom and forms a six-membered aromatic heterocyclic ring; and n represents an integer of from 1 to 3.

In Formula (I), the alkyl group represented by $R^1$ has 1 to 20 carbon atoms. From the viewpoint of solubility in organic solvents, the alkyl group represented by $R^1$ preferably has 1 to 12 carbon atoms, and more preferably 4 to 8 carbon atoms.

The alkyl group represented by $R^1$ may be any of a straight chain, a branched chain and a cyclic group. From the viewpoint of solubility in organic solvents, it is preferably a straight-chain alkyl group.

The alkyl group represented by $R^1$ may have a substituent, examples of which include halogen atoms (such as chlorine, bromine and fluorine atoms) and the like.

While the alkyl group represented by $R^1$ may have a substituent, it is preferably an unsubstituted alkyl group from the viewpoint of delivering hole transporting performance and increasing solubility.

In Formula (I), the alkoxy group represented by $R^1$ has 1 to 20 carbon atoms. From the viewpoint of solubility in organic solvents, the alkoxy group represented by $R^1$ preferably has 1 to 12 carbon atoms, and more preferably 4 to 8 carbon atoms.

The alkoxy group represented by $R^1$ may be any of a straight chain, a branched chain and a cyclic group. From the viewpoint of solubility in organic solvents, it is preferably a straight-chain alkoxy group.

The alkoxy group represented by $R^1$ may have a substituent, examples of which include halogen atoms (such as chlorine, bromine and fluorine atoms) and the like.

While the alkoxy group represented by $R^1$ may have a substituent, it is preferably an unsubstituted alkoxy group from the viewpoint of solubility, crystallinity, hole transporting properties, or the like.

Among these, $R^1$ in Formula (I) is preferably a hydrogen atom or a substituted or unsubstituted alkyl group having 1 to 20 carbon atoms, more preferably a hydrogen atom or an unsubstituted alkyl group having 1 to 20 carbon atoms, still more preferably an unsubstituted alkyl group having 1 to 12 carbon atoms, and furthermore preferably an unsubstituted straight-chain alkyl group having 4 to 8 carbon atoms.

In Formula (I), the substituent $R^1$ is preferably in 3- or 4-position of the benzene ring, more preferably in 4-position of the benzene ring, relative to the thiophene ring which is in 1-position), from the viewpoint of hole transporting performance.

In Formula (I), n represents an integer of from 1 to 3, and preferably 1 or 2.

In Formula (I), A represents a heterocyclic residue that contains at least one nitrogen atom and forms a six-membered aromatic heterocyclic ring. The six-membered aromatic heterocyclic ring formed by the A residue is preferably triazine, a triazine derivative, pyrazine, or a pyrazine derivative, from the viewpoint of delivering charge transporting performance.

Therefore, the compound represented by Formula (I) is preferably a pyrazine derivative represented by Formula (II) below or a triazine derivative represented by Formula (III) below.

(II)

In Formula (II), $R^1$ represents a hydrogen atom, a substituted or unsubstituted alkyl group having 1 to 20 carbon atoms or a substituted or unsubstituted alkoxy group having 1 to 20 carbon atoms; and n each independently represent an integer of from 1 to 3.

$R^1$ and n in Formula (II) have the same meaning and preferred range as $R^1$ and n in Formula (I).

The pyrazine derivative represented by Formula (II) has thiophene groups introduced in 2- and 6-positions of the pyrazine ring. The pyrazine derivative represented by Formula (II) having such a structure has high solubility in organic solvents and improved film-forming ability. Particularly when $R^1$ is an alkyl group having 1 to 12 carbon atoms, it has higher solubility in organic solvents, and when the alkyl group is unsubstituted, it is particularly suitable as a hole transporting material.

The pyrazine derivative represented by Formula (II) having thiophene groups introduced in 2- and 6-positions of the pyrazine ring also has good molecular orientation, when formed into a thin film.

(III)

In Formula (III), $R^1$ represents a hydrogen atom, a substituted or unsubstituted alkyl group having 1 to 20 carbon atoms or a substituted or unsubstituted alkoxy group having 1 to 20 carbon atoms; $R^2$ represents a hydrogen atom, a substituted or unsubstituted alkyl group having 1 to 10 carbon atoms, a substituted or unsubstituted alkoxy group having 1 to 10 carbon atoms, a substituted or unsubstituted aryl group having 6 to 10 carbon atoms, or a substituted or unsubstituted aryloxy group having 6 to 10 carbon atoms; and n represents an integer of from 1 to 3.

$R^1$ and n in Formula (III) have the same meaning and preferred range as $R^1$ and n in Formula (I).

In Formula (III), the alkyl group represented by $R^2$ has 1 to 10 carbon atoms. From the viewpoint of solubility in organic solvents, the alkyl group represented by $R^2$ preferably has 1 to 4 carbon atoms.

The alkyl group represented by $R^2$ may be any of a straight chain, a branched chain and a cyclic group, and it is preferably a straight-chain alkyl group from the viewpoint of solubility in organic solvents.

The alkyl group represented by $R^2$ may have a substituent, examples of which include halogen atoms (such as chlorine, bromine and fluorine atoms) and the like.

While the alkyl group represented by $R^2$ may have a substituent, it is preferably an unsubstituted alkyl group from the viewpoint of solubility in organic solvents.

In Formula (III), the alkoxy group represented by $R^2$ has 1 to 10 carbon atoms. From the viewpoint of solubility in organic solvents, the alkoxy group represented by $R^2$ preferably has 1 to 4 carbon atoms, and is more preferably a methoxy group.

While the alkoxy group represented by $R^2$ may be any of a straight chain, a branched chain and a cyclic group, it is preferably a straight-chain alkoxy group from the viewpoint of solubility in organic solvents.

The alkoxy group represented by $R^2$ may have a substituent, examples of which include halogen atoms (such as chlorine, bromine and fluorine atoms) and the like.

While the alkoxy group represented by $R^2$ may have a substituent, it is preferably an unsubstituted alkoxy group from the viewpoint of solubility in organic solvents.

In Formula (III), the aryl group represented by $R^2$ has 6 to 10 carbon atoms. From the viewpoint of solubility in organic solvents, the aryl group represented by $R^2$ is more preferably a phenyl group.

The aryl group represented by $R^2$ may have a substituent, examples of which include an alkyl group, a halogen atom group and the like. The substituent is preferably an alkyl group having 1 to 10 carbon atoms.

In Formula (III), the aryloxy group represented by $R^2$ has 6 to 10 carbon atoms. From the viewpoint of solubility in organic solvents, the aryloxy group represented by $R^2$ is more preferably a phenoxy group.

The aryloxy group represented by $R^2$ may have a substituent, examples of which include an alkyl group, a halogen atom group and the like. The substituent is preferably an alkyl group having 1 to 10 carbon atoms.

Among these, $R^2$ in Formula (III) is preferably a substituted or unsubstituted alkoxy group having 1 to 10 carbon atoms, more preferably an unsubstituted alkoxy group having 1 to 10 carbon atoms, even more preferably an unsubstituted alkoxy group having 1 to 4 carbon atoms, still more preferably an unsubstituted straight-chain alkoxy group having 1 to 4 carbon atoms, and furthermore preferably a methoxy group.

The triazine derivative represented by Formula (III) has thiophene groups in 2- and 6-positions of the triazine ring. The compound represented by Formula (III) has high solubility in organic solvents and is useful for the production of electronic components by coating methods or the like, compared to compounds having thiophene groups in 2-, 4- and 6-positions of the triazine ring.

When $R^1$ in Formula (III) is an alkyl group having 1 to 12 carbon atoms, the triazine derivative represented by Formula (III) can have higher solubility in organic solvents.

The triazine derivative represented by Formula (III) has a phenyl group-substituted thiophene ring. Such a structure has excellent hole transporting properties.

The triazine derivative represented by Formula (III) also has excellent molecular orientation, when formed into a thin film.

The examples of the nitrogen-containing heterocyclic compound represented by Formula (I) are shown below, which include examples of the pyrazine derivative represented by Formula (II) shown in Table 1 below and examples of the triazine derivative represented by Formula (III) shown in Table 2 below. The examples shown below are not intended to limit the scope of the invention.

TABLE 1

| No | $R^1$ | Bond position | n |
|---|---|---|---|
| II-1 | H | — | 1 |
| II-2 | $CH_3$— | 3 | 1 |
| II-3 | $CH_3$— | 4 | 1 |
| II-4 | $C_2H_5$— | 3 | 1 |
| II-5 | $C_2H_5$— | 4 | 1 |
| II-6 | $CH_3(CH_2)_3$— | 4 | 1 |
| II-7 | $(CH_3)_3C$— | 4 | 1 |
| II-8 | $CH_3(CH_2)_5$— | 4 | 1 |
| II-9 | $CH_3(CH_2)_7$— | 4 | 1 |
| II-10 | $CH_3(CH_2)_3$— | 4 | 2 |
| II-11 | $CH_3(CH_2)_7$— | 4 | 2 |
| II-12 | $CH_3(CH_2)_{11}$— | 4 | 2 |
| II-13 | $CH_3(CH_2)_3$— | 4 | 3 |
| II-14 | $CH_3(CH_2)_7$— | 4 | 3 |
| II-15 | $CH_3O$— | 3 | 1 |
| II-16 | $CH_3O$— | 4 | 1 |
| II-17 | $C_2H_5O$— | 4 | 1 |
| II-18 | $CH_3(CH_2)_3O$— | 3 | 2 |
| II-19 | $CH_3(CH_2)_3O$— | 4 | 1 |
| II-20 | $CH_3(CH_2)_7O$— | 4 | 3 |

TABLE 2

| No. | $R^1$ | Bond position | n | $R^2$ |
|---|---|---|---|---|
| III-1 | H | — | 1 | $CH_3O$— |
| III-2 | $CH_3$— | 3 | 1 | $CH_3O$— |
| III-3 | $CH_3$— | 4 | 1 | $CH_3O$— |
| III-4 | $C_2H_5$— | 3 | 1 | $CH_3(CH_2)_2O$— |
| III-5 | $C_2H_5$— | 4 | 1 | $CH_3O$— |
| III-6 | $CH_3(CH_2)_3$— | 4 | 1 | H |
| III-7 | $CH_3(CH_2)_3$— | 4 | 1 | $CH_3O$— |
| III-8 | $(CH_3)_3C$— | 4 | 1 | $CH_3O$— |
| III-9 | $CH_3(CH_2)_5$— | 4 | 1 | $CH_3O$— |
| III-10 | $CH_3(CH_2)_7$— | 4 | 1 | $CH_3O$— |
| III-11 | $CH_3(CH_2)_3$— | 4 | 2 | $CH_3O$— |
| III-12 | $CH_3(CH_2)_7$— | 4 | 2 | $CH_3O$— |
| III-13 | $CH_3(CH_2)_{11}$— | 4 | 2 | $CH_3O$— |
| III-14 | $CH_3(CH_2)_3$— | 4 | 3 | $CH_3O$— |
| III-15 | $CH_3(CH_2)_7$— | 4 | 3 | $CH_3O$— |
| III-16 | $CH_3O$— | 3 | 1 | $CH_3O$— |
| III-17 | $CH_3O$— | 4 | 1 | $CH_3O$— |
| III-18 | $C_2H_5O$— | 4 | 2 | $CH_3O$— |
| III-19 | $CH_3(CH_2)_3O$— | 3 | 1 | H |
| III-20 | $CH_3(CH_2)_3O$— | 4 | 1 | $CH_3$— |
| III-21 | $CH_3(CH_2)_3O$— | 4 | 1 | $C_6H_5$— |
| III-22 | $CH_3(CH_2)_3O$— | 4 | 2 | $CH_3O$— |
| III-23 | $CH_3(CH_2)_3O$— | 3 | 1 | $C_6H_5O$— |
| III-24 | $CH_3(CH_2)_7O$— | 4 | 3 | $C_3O$— |

The nitrogen-containing heterocyclic compound represented by Formula (I) is useful as a charge transporting material and may be typically used for organic photoreceptors (electrophotographic photoreceptors) and organic electronic devices such as organic electroluminescence devices, organic transistors, organic solar cells, or organic memories.

EXAMPLES

The present invention is more specifically described by the examples below, which are not intended to limit the scope of the invention.

Method of Measuring Charge Mobility

In this example, the charge mobility of the object is measured by the Time-of-Flight method (using a TOF-401 manufactured by Optel Corporation, Ltd.; excitation light source: nitrogen pulsed laser (wavelength 337 nm); applied voltage: 30 V/μm). Unless otherwise stated, the charge mobility measurement is performed using a film of a dispersion containing 40% by mass of the object in polycarbonate.

Method of Measuring Ionization Potential

The ionization potential of the object is measured in the air using a photoelectron spectrometer (AC-2 manufactured by RIKEN KEIKI Co., Ltd.).

Method of Evaluating Solubility

The object is added into each of dichloroethane, toluene and chlorobenzene so that the concentration of the object is 2% by mass. After the mixture is stirred, the state of the resulting solution is visually observed for the evaluation of the solubility. The solvent species used are generally suitable for use in the preparation of electronic devices. The solubility is evaluated according to the criteria below.

A: In the visual inspection, the object is completely dissolved.
B: In the visual inspection, a small amount of the object is precipitated.
C: In the visual inspection, the object is almost insoluble, and a large amount of the object is precipitated.

Method of Identification

The object is identified by $^1$H-NMR spectroscopy ($^1$H-NMR UNITY-300 manufactured by Varian, Inc., 300 MHz, solvent $CDCl_3$) and IR spectroscopy (by KBr disk method with a Fourier transform infrared spectrophotometer (FT-730 manufactured by HORIBA, Ltd., resolution 4 cm$^{-1}$).

Example 1

Synthesis of Compound (II-6)

A solution including 4.0 g (27 mmol) of 2,6-dichloropyrazine (manufactured by Tokyo Chemical Industry Co., Ltd.),

7.5 g (59 mmol) of 2-thiopheneboronic acid (manufactured by Tokyo Chemical Industry Co., Ltd.), and 0.43 g (0.37 mmol) of tetrakis(triphenylphosphine)palladium(0) (hereinafter also referred to as Pd(PPh$_3$)$_4$, manufactured by Tokyo Chemical Industry Co., Ltd.) in 150 ml of tetrahydrofuran is prepared, and a solution including 14.5 g of sodium carbonate (manufactured by Wako Pure Chemical Industries, Ltd.) in 60 ml of water is added thereto. The resulting mixture is stirred at 60° C. for 6 hours under a nitrogen stream.

After allowed to cool, the mixture is poured into 500 ml of water, and the resulting precipitate is separated by filtration and washed with water. The precipitate is dried under reduced pressure and then dissolved in toluene. Impurities are removed from the solution by column chromatography (silica gel), and recrystallization from a toluene/methanol mixed solvent is preformed, so that 3.3 g of 2,6-bis(2'-thienyl)pyrazine is obtained (50% of the theoretical yield).

A solution including 3.0 g (12 mmol) of the resulting 2,6-bis(2'-thienyl)pyrazine in 80 ml of N,N-dimethylformamide is prepared, and 5.5 g (31 mmol) of N-bromosuccinimide (hereinafter also referred to as NBS, manufactured by Wako Pure Chemical Industries, Ltd.) is added thereto. The resulting mixture is stirred at 80° C. for 5 hours under a nitrogen stream.

After allowed to cool, the mixture is poured into 500 ml of water, and the resulting precipitate is separated by filtration and washed with water The precipitate is dried under reduced pressure and then recrystallized from a toluene/methanol mixed solvent, so that 2.45 g of 2,6-bis(5'-bromo-2'-thienyl)pyrazine is obtained (49% of the theoretical yield).

A solution including 0.52 g (1.3 mmol) of the resulting 2,6-bis(5'-bromo-2'-thienyl)pyrazine, 0.51 g (2.9 mmol) g of 4-n-butylbenzeneboronic acid (manufactured by Wako Pure Chemical Industries, Ltd.), and 0.017 g (0.015 mmol) of tetrakis(triphenylphosphine)palladium(0) (manufactured by Tokyo Chemical Industry Co., Ltd.) in 25 ml of N-methylpyrrolidone is prepared, and a solution including 0.80 g (6.8 mmol) of sodium carbonate (manufactured by Wako Pure Chemical Industries, Ltd.) in 5 ml of water is added thereto. The resulting mixture is stirred at 80° C. for 6 hours.

After allowed to cool, the mixture is poured into 400 ml of water, and the resulting precipitate is separated by filtration and washed with water. The precipitate is dried under reduced pressure and then dissolved in toluene. The dissolved precipitate is purified by column chromatography (silica gel) and recrystallized from a toluene/methanol mixed solvent, so that 0.45 g of compound (II-6) is obtained (69% of the theoretical yield).

The resulting compound (II-6) has a melting point of 152° C. to 152.5° C.

Figure 1:
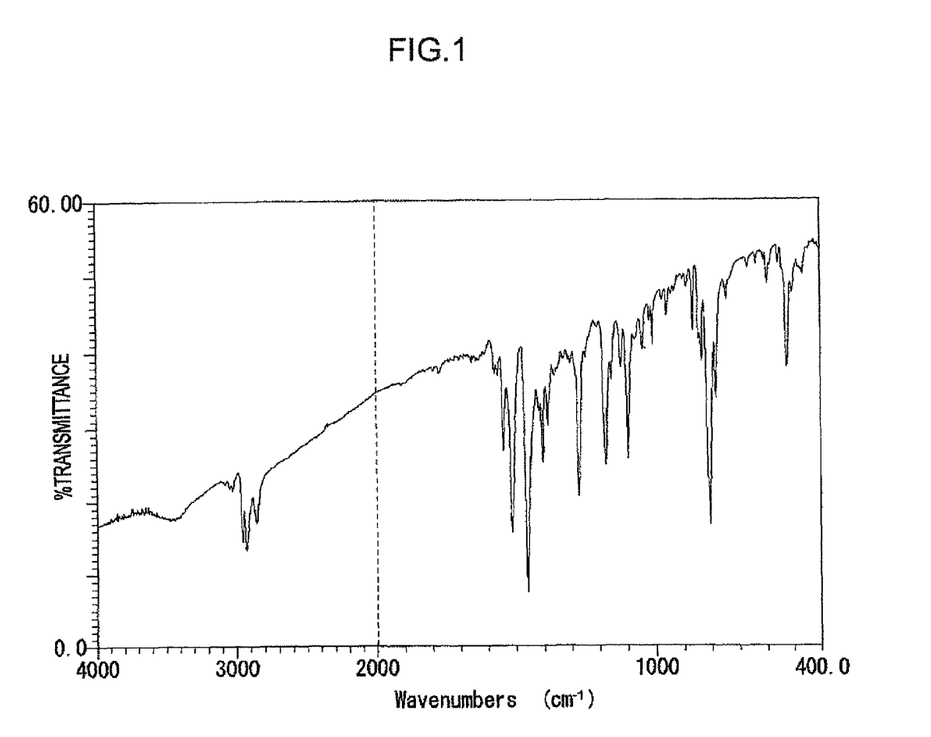
FIG. 1 is the infrared absorption spectrum of the compound obtained in Example 1.
Figure 2:
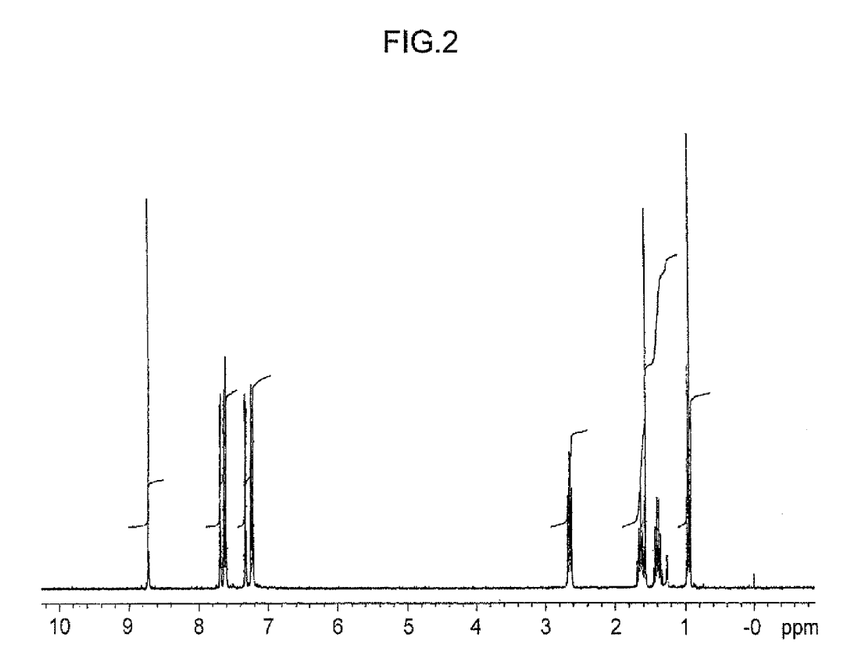
FIG. 2 is the NMR spectrum of the compound obtained in Example 1.

The infrared absorption spectrum and $^1$H-NMR spectrum of the resulting compound (II-6) are shown in FIGS. 1 and 2, respectively.

(II-6)

Example 2

Synthesis of Compound (II-11)

A solution including 3.8 g (9.4 mmol) of 2,6-bis(5'-bromo-2'-thienyl)pyrazine obtained using the process of Example 1, 2.7 g (21 mmol) of 2-thiopheneboronic acid (manufactured by Tokyo Chemical Industry Co., Ltd.), and 0.18 g (0.16 mmol) of tetrakis(triphenylphosphine)palladium(0) (manufactured by Tokyo Chemical Industry Co., Ltd.) in 200 ml of N,N-dimethylformamide is prepared, and a solution including 5.7 g (48 mmol) of sodium carbonate (manufactured by Wako Pure Chemical Industries, Ltd.) in 30 ml of water is added thereto. The resulting mixture is stirred at 90° C. to 100° C. for 4 hours.

After allowed to cool, the mixture is poured into 700 ml of water, and the resulting precipitate is separated by filtration and washed with water. The precipitate is dried under reduced pressure and then dissolved in toluene. The dissolved precipitate is purified by column chromatography (silica gel) and recrystallized from a toluene/methanol mixed solvent, so that 1.8 g of 2,6-bis(2',2"-bithiophene-5'-yl)pyrazine is obtained (47% of the theoretical yield).

A solution including 1.36 g (12 mmol) of the resulting 2,6-bis(2',2''-bithiophene-5'-yl)pyrazine in 80 ml of N,N-dimethylformamide is prepared, and 1.33 g (31 mmol) of N-bromosuccinimide (manufactured by Wako Pure Chemical Industries, Ltd.) is added thereto. The resulting mixture is stirred at 70° C. for 5 hours under a nitrogen stream. After allowed to cool, the mixture is poured into 500 ml of water, and the resulting precipitate is separated by filtration and washed with water. The precipitate is dried under reduced pressure and then recrystallized from a toluene/methanol mixed solvent, so that 1.43 g of 2,6-bis(5''-bromo-2',2''-bithiophene-5'-yl)pyrazine is obtained (76% of the theoretical yield).

A solution including 1.0 g (0.18 mmol) of the resulting 2,6-bis(5''-bromo-2',2''-bithiophene-5'-yl)pyrazine, 1.0 g (0.44 mmol) of 4-n-octylbenzeneboronic acid (manufactured by Tokyo Chemical Industry Co., Ltd.), and 0.076 g (0.066 mmol) of tetrakis(triphenylphosphine)palladium(0) in 200 ml of N-methylpyrrolidone is prepared, and a solution including 1.4 g (1.2 mmol) of sodium carbonate (manufactured by Wako Pure Chemical Industries, Ltd.) in 5 ml of water is added thereto. The resulting mixture is stirred at 100° C. for 6 hours in a nitrogen stream.

After allowed to cool, the mixture is poured into 800 ml of water, and the resulting precipitate is separated by filtration and washed with water. The precipitate is dried under reduced pressure and then dissolved in toluene. The dissolved precipitate is purified by column chromatography (silica gel) and recrystallized from toluene, so that 0.23 g of compound (II-11) is obtained (16% of the theoretical yield).

The resulting compound (II-11) has a melting point of 197.5° C. to 199° C.

Figure 3:
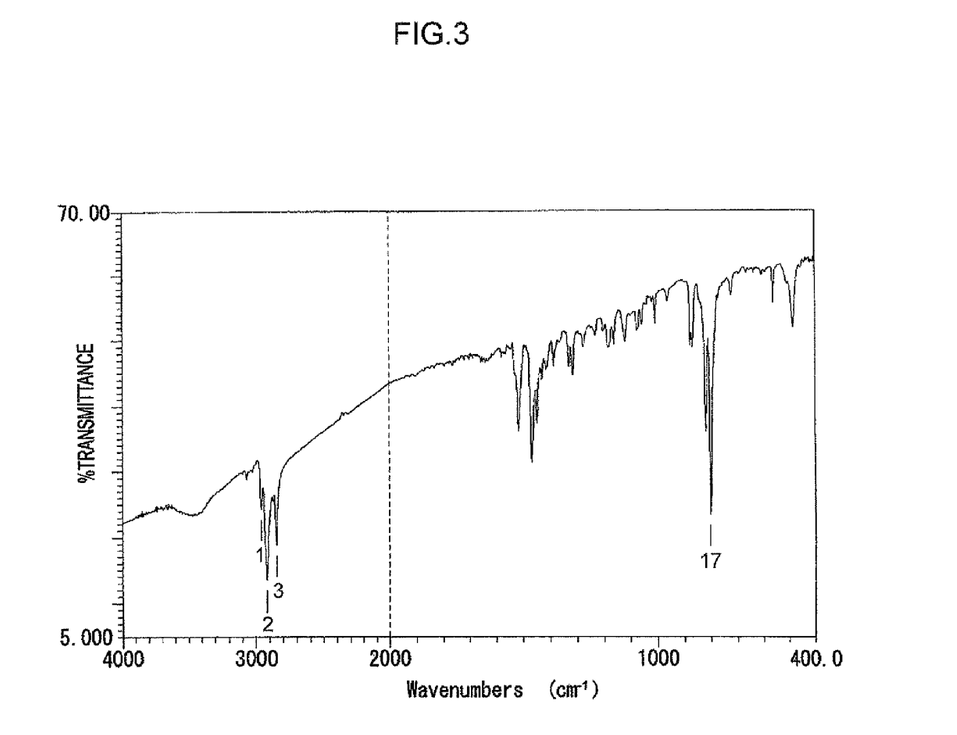
FIG. 3 is the infrared absorption spectrum of the compound obtained in Example 2.
Figure 4:
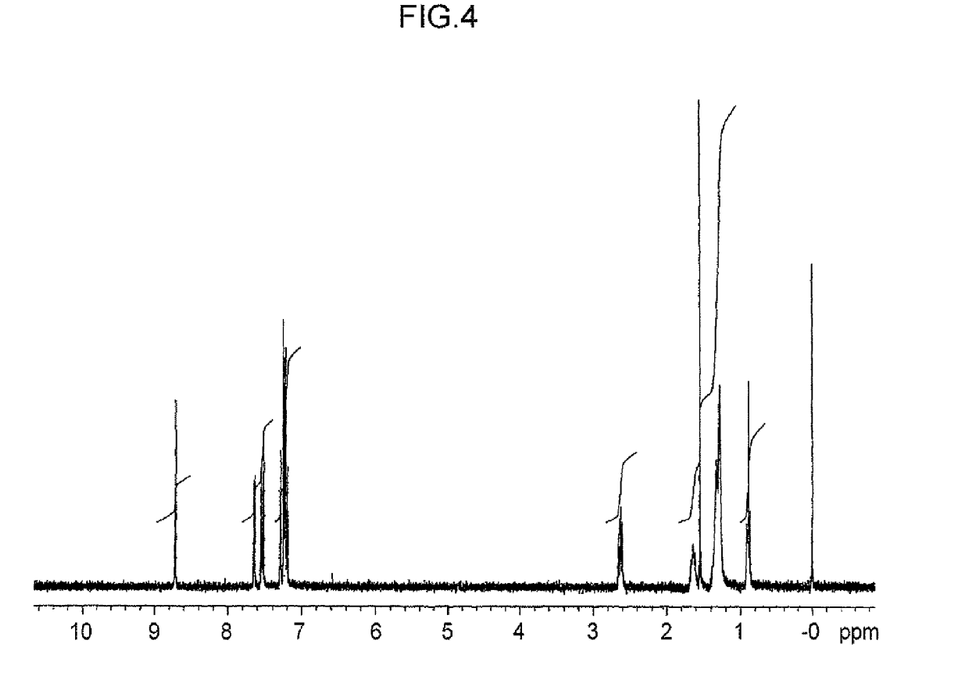
FIG. 4 is the NMR spectrum of the compound obtained in Example 2.

The infrared absorption spectrum and $^1$H-NMR spectrum of the resulting compound (II-11) are shown in FIGS. 3 and 4, respectively.

(II-11)

Example 3

Synthesis of Compound (III-7)

A solution including 4.0 g (22 mmol) of 2,4-dichloro-6-methoxy-1,3,5-triazine (manufactured by Sigma-Aldrich Corporation), 6.2 g (48 mmol) of 2-thiopheneboronic acid (manufactured by Tokyo Chemical Industry Co., Ltd.), and 0.10 g (0.09 mmol) of tetrakis(triphenylphosphine)palladium (0) in 160 ml of tetrahydrofuran is prepared, and a solution including 12.3 g of sodium carbonate (manufactured by Wako Pure Chemical Industries, Ltd.) in 50 ml of water is added thereto. The resulting mixture is stirred at 60° C. for 6 hours under a nitrogen stream.

After allowed to cool, the mixture is poured into 800 ml of water, and the oil-soluble component is extracted with ethyl acetate. After the extract is concentrated under reduced pressure, impurities are removed from the concentrate by column chromatography (silica gel). The concentrate is further recrystallized from a toluene/methanol mixed solvent, so that 4.55 g of 2,4-bis(2'-thienyl)-6-methoxy-1,3,5-triazine is obtained (74% of the theoretical yield).

A solution including 4.0 g (9.6 mmol) of the resulting 2,4-bis(2'-thienyl)-6-methoxy-1,3,5-triazine in 50 ml of N,N-dimethylformamide is prepared, and 6.2 g (35 mmol) of N-bromosuccinimide (manufactured by Wako Pure Chemical Industries, Ltd.) is added thereto. The resulting mixture is stirred at 80° C. for 5 hours under a nitrogen stream.

After allowed to cool, the mixture is poured into 800 ml of water, and the resulting precipitate is separated by filtration and washed with water The precipitate is dried under reduced pressure and then recrystallized from a toluene/methanol mixed solvent, so that 2.45 g of 2,4-bis(5'-bromo-2'-thienyl)-6-methoxy-1,3,5-triazine is obtained (49% of the theoretical yield).

A solution including 1.03 g (1.3 mmol) of the resulting 2,4-bis(5'-bromo-2'-thienyl)-6-methoxy-1,3,5-triazine, 1.0 g of 4-n-butylbenzeneboronic acid (manufactured by Wako Pure Chemical Industries, Ltd.), and 0.021 g (0.018 mmol) of tetrakis(triphenylphosphine)palladium(0) (manufactured by Tokyo Chemical Industry Co., Ltd.) in 60 ml of N-methylpyrrolidone is prepared, and a solution including 3.0 g (6.8 mmol) of sodium carbonate (manufactured by Wako Pure Chemical Industries, Ltd.) in 15 ml of water is added thereto. The resulting mixture is stirred at 90° C. for 6 hours under a nitrogen stream.

After allowed to cool, the mixture is poured into 400 ml of water, and the resulting precipitate is separated by filtration and washed with water. The precipitate is dried under reduced pressure and then dissolved in toluene. The dissolved precipitate is purified by column chromatography (silica gel) and recrystallized from a toluene/methanol mixed solvent, so that 0.80 g of compound (III-7) is obtained (62% of the theoretical yield).

The resulting compound (III-7) has a melting point of 140° C. to 141° C.

Figure 5:
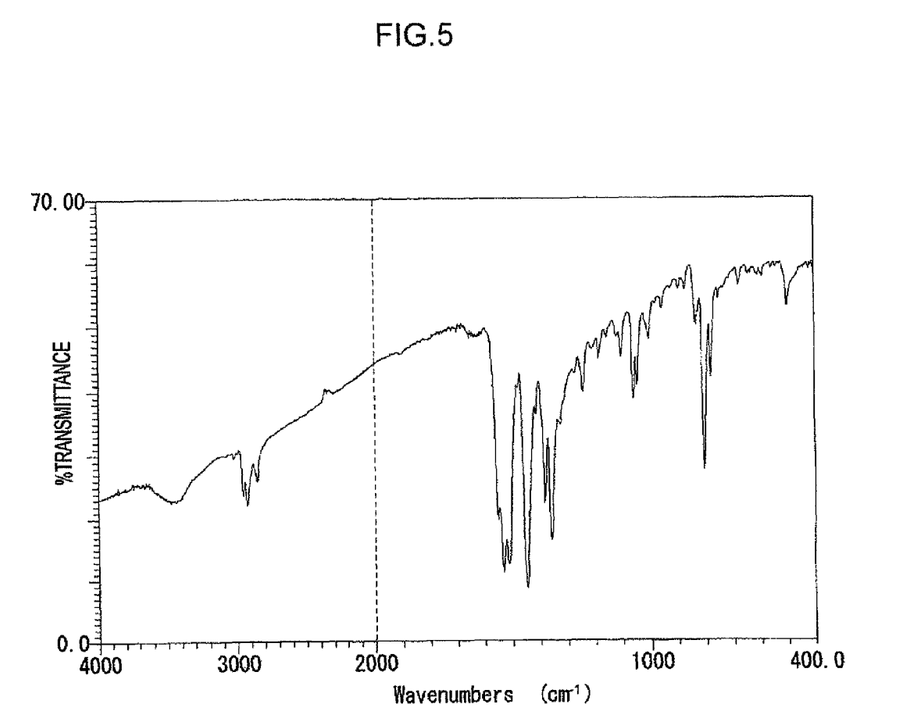
FIG. 5 is the infrared absorption spectrum of the compound obtained in Example 3.
Figure 6:
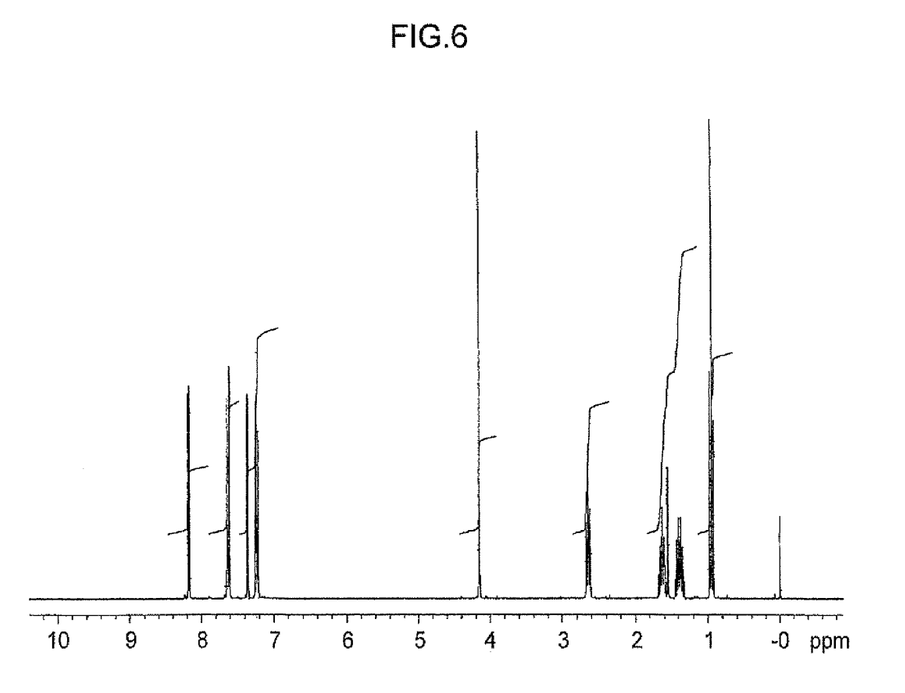
FIG. 6 is the NMR spectrum of the compound obtained in Example 3.

The infrared absorption spectrum and $^1$H-NMR spectrum of the resulting compound (II-7) are shown in FIGS. 5 and 6, respectively.

Example 4

Synthesis of Compound (III-11)

A solution including 1.1 g (2.6 mmol) of 2,4-bis(5'-bromo-2'-thienyl)-6-methoxy-1,3,5-triazine obtained using the process of Example 3, 1.0 g (8.0 mmol) of 2-thiopheneboronic acid (manufactured by Tokyo Chemical Industry Co., Ltd.), and 0.04 g (0.035 mmol) of tetrakis(triphenylphosphine)palladium(0) (manufactured by Tokyo Chemical Industry Co., Ltd.) in 40 ml of N-methylpyrrolidone is prepared, and a solution including 3.0 g (6.8 mmol) of sodium carbonate (manufactured by Wako Pure Chemical Industries, Ltd.) in 15 ml of water is added thereto. The resulting mixture is stirred at 80° C. for 4 hours in a nitrogen stream.

After allowed to cool, the mixture is poured into 400 ml of water, and the resulting precipitate is separated by filtration and washed with water. The precipitate is dried under reduced pressure and then dissolved in toluene. The dissolved precipitate is purified by column chromatography (silica gel) and recrystallized from a toluene/methanol mixed solvent, so that 0.78 g of 2,4-bis(2',2''-bithiophene-5'-yl)-6-methoxy-1,3,5-triazine is obtained (71% of the theoretical yield).

A solution including 0.76 g (1.8 mmol) of the resulting 2,4-bis(2',2''-bithiophene-5'-yl)-6-methoxy-1,3,5-triazine in 35 ml of N,N-dimethylformamide is prepared, and 0.68 g (3.8 mmol) of N-bromosuccinimide (manufactured by Wako Pure Chemical Industries, Ltd.) is added thereto. The resulting mixture is stirred at 70° C. for 3 hours under a nitrogen stream.

After allowed to cool, the mixture is poured into 400 ml of water, and the resulting precipitate is separated by filtration and washed with water. The precipitate is dried under reduced pressure and then recrystallized from a toluene/methanol mixed solvent, so that 0.71 g of 2,4-bis(5''-bromo-2',2''-bithiophene-5'-yl)-6-methoxy-1,3,5-triazine is obtained (68% of the theoretical yield).

A solution including 0.65 g (1.1 mmol) of the resulting 2,4-bis(5''-bromo-2',2''-bithiophene-5'-yl)-6-methoxy-1,3,5-triazine, 0.45 g (2.5 mmol) of 4-n-butylbenzeneboronic acid (manufactured by Wako Pure Chemical Industries, Ltd.), and 0.014 g (0.012 mmol) of tetrakis(triphenylphosphine)palladium(0) (manufactured by Tokyo Chemical Industry Co., Ltd.) in 80 ml of N-methylpyrrolidone is prepared, and a solution including 0.61 g (5.2 mmol) of sodium carbonate (manufactured by Wako Pure Chemical Industries, Ltd.) in 4 ml of water is added thereto. The resulting mixture is stirred at 90° C. for 6 hours.

After allowed to cool, the mixture is poured into 500 ml of water, and the resulting precipitate is separated by filtration and washed with water. The precipitate is dried under reduced pressure and then dissolved in toluene. The dissolved precipitate is purified by column chromatography (silica gel) and recrystallized from toluene, so that 0.22 g of compound (III-11) is obtained (30% of the theoretical yield).

The resulting compound (III-11) has a melting point of 171° C. to 173° C.

Figure 7:
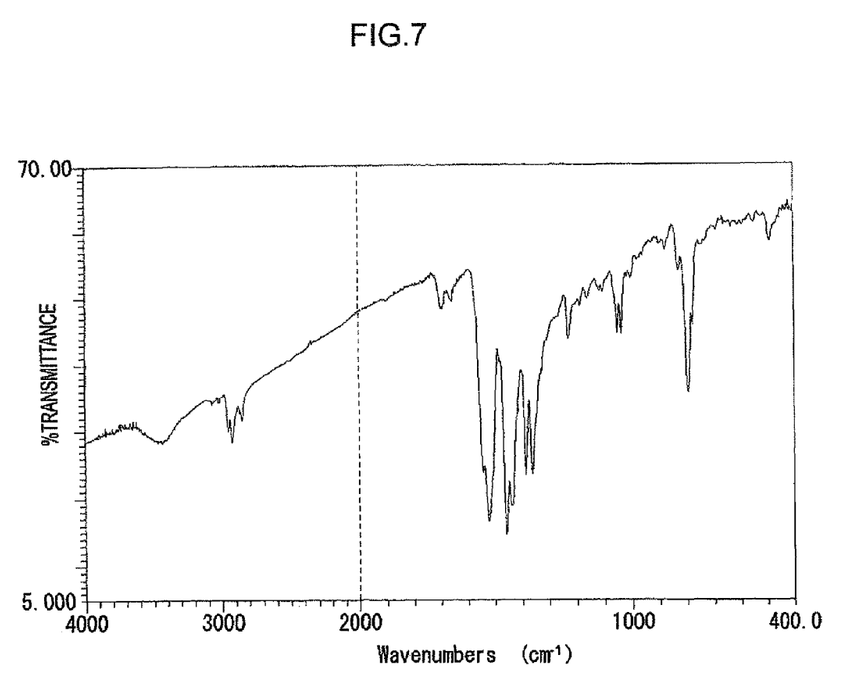
FIG. 7 is the infrared absorption spectrum of the compound obtained in Example 4.
Figure 8:
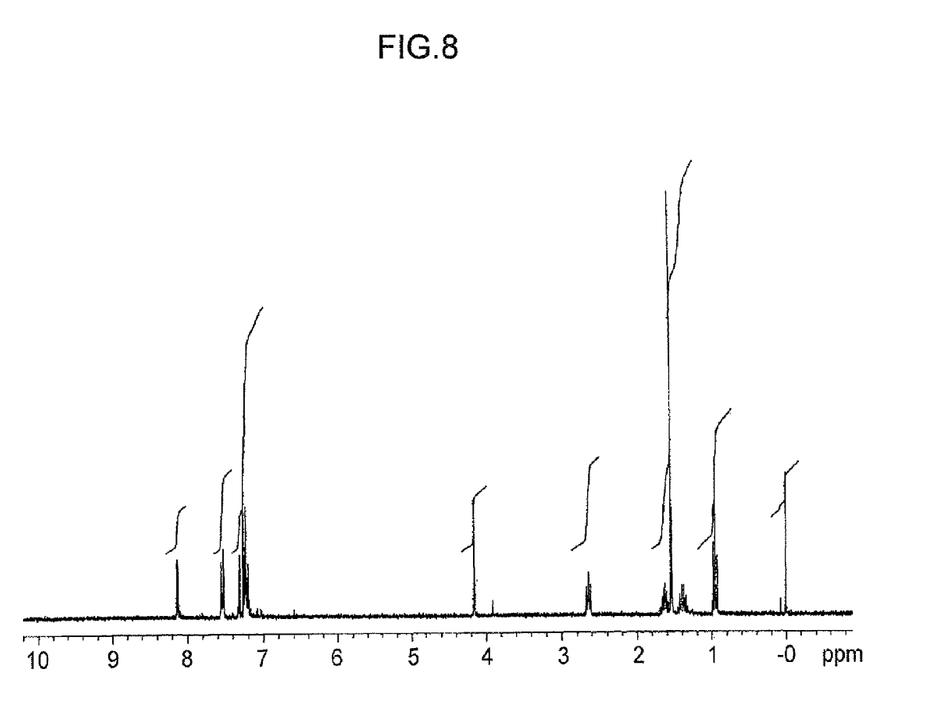
FIG. 8 is the NMR spectrum of the compound obtained in Example 4.

The infrared absorption spectrum and $^1$H-NMR spectrum of the resulting compound (III-11) are shown in FIGS. 7 and 8, respectively.

TABLE 3

| Compound | | Charge Mobility ($cm^2/Vs$) | Ionization Potential (eV) | Solubility | | |
|---|---|---|---|---|---|---|
| | | | | Dichloroethane | Toluene | Chlorobenzene |
| Example 1 | II-6 | $2.2 \times 10^{-6}$ | 5.76 | A | A | A |
| Example 2 | II-11 | $1.7 \times 10^{-5}$ | 5.40 | A | B | A |
| Example 3 | III-7 | $5.6 \times 10^{-7}$ | 5.85 | A | A | A |
| Example 4 | III-11 | $1.1 \times 10^{-5}$ | 5.52 | A | A | A |

The nitrogen-containing heterocyclic compounds of Examples 1 to 4 each have high charge transporting properties and high solubility in organic solvents suitable for use in the preparation of electronic devices. Therefore, they are useful as materials for organic photoreceptors and organic electronic devices such as organic electroluminescence devices and organic transistors.

The foregoing description of the embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A nitrogen-containing heterocyclic compound represented by the following formula:

wherein $R^1$ represents a hydrogen atom, a substituted or unsubstituted alkyl group having 1 to 20 carbon atoms, or a substituted or unsubstituted alkoxy group having 1 to 20 carbon atoms; $R^2$ represents a hydrogen atom, a substituted or unsubstituted alkyl group having 1 to 10 carbon atoms, a substituted or unsubstituted alkoxy group having 1 to 10 carbon atoms, a substituted or unsubstituted aryl group having 6 to 10 carbon atoms, or a substituted or unsubstituted aryloxy group having 6 to 10 carbon atoms; and n represents an integer of from 1 to 3.

2. The nitrogen-containing heterocyclic compound according to claim 1, wherein $R^1$ is an unsubstituted alkyl group.

3. The nitrogen-containing heterocyclic compound according to claim 1, wherein $R^1$ is a straight-chain alkyl group.

4. The nitrogen-containing heterocyclic compound according to claim 1, wherein $R^1$ is a straight-chain alkoxy group.

5. The nitrogen-containing heterocyclic compound according to claim 1, wherein $R^1$ is an unsubstituted alkoxy group.

6. The nitrogen-containing heterocyclic compound according to claim 1, wherein the substituent $R^1$ is in 3- or 4-positions of the benzene ring, relative to the thiophene ring which is in 1-position.

7. The nitrogen-containing heterocyclic compound according to claim 1, wherein $R^2$ is an unsubstituted alkyl group.

8. The nitrogen-containing heterocyclic compound according to claim 1, wherein $R^2$ is a straight-chain alkyl group.

9. The nitrogen-containing heterocyclic compound according to claim 1, wherein $R^2$ is a straight-chain alkoxy group.

10. The nitrogen-containing heterocyclic compound according to claim 1, wherein $R^2$ is an unsubstituted alkoxy group.

11. The nitrogen-containing heterocyclic compound according to claim 1, wherein $R^1$ is an alkyl group having 1 to 12 carbon atoms, and $R^2$ is an alkoxy group having 1 to 4 carbon atoms.

* * * * *